(12) United States Patent
Stevanato et al.

(10) Patent No.: US 12,061,158 B2
(45) Date of Patent: Aug. 13, 2024

(54) DEVICE AND METHOD FOR MEASURING THE WATER CONTENT OF THE GROUND, VEGETATION AND SNOW

(71) Applicant: Universita' degli Studi di Padova, Padua (IT)

(72) Inventors: Luca Stevanato, Padua (IT); Marcello Lunardon, Padua (IT); Sandra Moretto, Padua (IT); Cristiano Lino Fontana, Padua (IT)

(73) Assignee: Universita' degli Studi di Padova, Padua (IT)

( * ) Notice: Subject to any disclaimer, the term of this patent is extended or adjusted under 35 U.S.C. 154(b) by 386 days.

(21) Appl. No.: 17/420,264

(22) PCT Filed: Dec. 23, 2019

(86) PCT No.: PCT/IB2019/061282
§ 371 (c)(1),
(2) Date: Jul. 1, 2021

(87) PCT Pub. No.: WO2020/141406
PCT Pub. Date: Jul. 9, 2020

(65) Prior Publication Data
US 2022/0091052 A1 Mar. 24, 2022

(30) Foreign Application Priority Data
Jan. 4, 2019 (IT) .................. 102019000000076

(51) Int. Cl.
*G01N 23/09* (2018.01)
*G01N 33/00* (2006.01)
(Continued)

(52) U.S. Cl.
CPC ......... *G01N 23/09* (2013.01); *G01N 33/0098* (2013.01); *G01N 33/246* (2013.01);
(Continued)

(58) Field of Classification Search
None
See application file for complete search history.

(56) References Cited

U.S. PATENT DOCUMENTS

| 2014/0151566 | A1* | 6/2014 | Ramsden | ............... G01T 3/001 250/366 |
| 2015/0241579 | A1  | 8/2015 | Menge   | |
| 2019/0178818 | A1* | 6/2019 | Zreda   | ................ G01T 7/00 |

OTHER PUBLICATIONS

Steinmetz, Johannes, "International Search Report and Written Opinion of the international Searching Authority for International Application No. PCT/IB2019/061282," European Patent Office, Apr. 22, 2020.
(Continued)

*Primary Examiner* — Hoon K Song
(74) *Attorney, Agent, or Firm* — Florek & Endres PLLC

(57) ABSTRACT

A device (12) for measuring the water content of the ground, vegetation and snow, comprises: at least one first module (20) adapted to measure a flow of cosmic rays incident to the ground; at least one second module (40) adapted to measure an ambient neutron flow; and a control unit (60) connected to said at least one first module (20) and said at least one second module (40). The control unit (60) is adapted to process the measurements of said at least one first module (20) and said at least one second module (40) to determine the measurement of the water content.

19 Claims, 6 Drawing Sheets

(51) Int. Cl.
*G01N 33/24* (2006.01)
*G01T 3/06* (2006.01)
*G01N 33/18* (2006.01)

(52) U.S. Cl.
CPC ............ *G01T 3/06* (2013.01); *G01N 33/1873* (2024.05); *G01N 33/245* (2024.05); *G01N 2223/5055* (2013.01)

(56) References Cited

OTHER PUBLICATIONS

M Zreda et al, "COSMOS: the COsmic-ray Soil Moisture Observing System", DOI: 10.5194/hess-16-4079-2012 Nov. 7, 2012 (Nov. 7, 2012), p. 4079-4099, Retrieved from the Internet: URL:https://www.hydrol-earth-syst-sci.net/16/4079/2012/hess-16-4079-2012.pdf XP055628520 DOI: 10.5194/hess-16-4079-2012 [retrieved on Oct. 3, 2019].

Cester D et al, "A novel detector assembly for detecting thermal neutrons, fast neutrons and gamma rays", Nuclear Instruments & Methods in Physics Research. Section A, Elsevier BV North-Holland, NL, vol. 830, May 24, 2016 (May 24, 2016), p. 191-196, XP029652597 DOI: 10.1016/J.NIMA.2016.05.079 ISSN:0168-9002.

Stoykov A et al, "A SiPM-based ZnS:/\6LiF scintillation neutron detector", arxiv.org, Cornell University Library, 201 Olin Library Cornell University Ithaca, NY 14853,Aug. 26, 2014 (Aug. 26, 2014), XP081391275 DOI: 10.1016/J.NIMA.2015.01.076 ISSN:1742-6596.

Carturan S M et al, "Thermal neutron detection by entrappingLiF nanocrystals in siloxane scintillators", Jun. 11, 2015 (Jun. 11, 2015), vol. 620, No. 1, p. 12010, XP020286138 DOI: 10.1088/1742-6596/620/1/012010.

Schrön M et al, "Intercomparison of cosmic-ray neutron sensors and water balance monitoring in an urban environment", Geoscientific Instrumentation, Methods and Data Systems, 7, 83-99, 2018 https://doi.org/10.5194/gi-7-83-2018.

\* cited by examiner

DEVICE AND METHOD FOR MEASURING THE WATER CONTENT OF THE GROUND, VEGETATION AND SNOW

FIELD OF APPLICATION

The present invention relates to a device and a method for measuring the water content of the ground, vegetation and snow. In particular, the present invention relates to a device and a method for measuring the water content of the ground, vegetation and snow on a large scale.

BACKGROUND ART

As is known, water content measurements may be made by using different types of devices.

For example, the measurement of the water content of the ground is known by using punctual probes of the electromagnetic type, from which it is possible to obtain an indication relating to a terrain volume of about one dm3.

There are also systems which employ remote sensing and use images originating from satellites or drones. The information detected, with the ones available from weather stations or other centers which provide databases relating to climatology, are then correlated by means of mathematical models.

Some attempts to apply a technology based on the measurement of ambient neutrons induced by cosmic rays on the ground are also known. In fact, it has been shown that there is a fairly clear correlation between neutron flow and the average water content of the ground, vegetation and snow.

As known, the production of energy neutrons between epithermal and slow (0.5 eV-1 keV) is influenced on a regular basis by the presence of hydrogen, which, in turn, is directly connected to the water content. This information, suitably processed by mathematical models, is adapted to respond to the need to know in real time (with an hourly to daily frequency) the water availability condition of cultivated land, snow and vegetation. Furthermore, this measurement provides averaged information on an area extended up to a few hectares, and up to a depth of about 50-60 cm.

An example of a mathematical model which may be used for converting the ambient neutron data acquired into ground water content, is described in "Geoscientific Instrumentation Methods and Data Systems" 7, 83-99, 2018 by the authors Schron at al.

To date, some types of ambient neutron detectors are available, which are adapted for this type of application.

Current probes are based on gas detection technologies (e.g., Helium-3, Boron-10) which imply high production and sales prices, probably not destined to decrease, but rather to increase. Such probes are optimized for research and not for a continuous use in agriculture and/or environmental monitoring.

For these reasons, these types of probes are currently only used in scientific research projects.

The background art, although employed and appreciated, is therefore not without drawbacks.

For example, in the case of punctual measurements with electromagnetic probes, a very large number of probes would be needed to monitor hundreds or thousands of cultivated hectares or land with a high degree of inhomogeneity, effectively making the monitoring uneconomical.

In the case of remote sensing, the limitations are due to several aspects, including:

the defined periodicity of satellite images (low is about one image a week, in the case of higher resolution images) and the possibility that such images are locally obscured by clouds;

legal and practical limits in the use of detections with drones;

difficulties in correlating the information extracted from the images and the ground water content actually available for vegetation. During plant growth, aerial images essentially evaluate, in the best of cases, the state of the vegetation, but do not have direct access to the situation of the underlying ground, and, in any case, the information only concerns the first centimeters of ground.

Finally, in the case of known systems which measure ambient neutrons, these are, as a matter of fact, too expensive to be economically advantageous.

Furthermore, ambient neutron flow, in addition to the humidity of the ground, is also dependent on the incident flow of cosmic rays which is variable depending on the geographical position, the time of the year and local weather conditions. Ambient neutron probes of the known type make use of data provided by some research centers around the world. The use of this data, however, is not very precise since it may be detected several hundred kilometers away and the usability thereof is not guaranteed in any way, since the data are made available at the discretion of the research center.

PRESENTATION OF THE INVENTION

The need to resolve the aforesaid drawbacks and limitations with reference to the background art is therefore felt.

Therefore, the need is felt to provide a device for measuring the water content which is more reliable with respect to the background art systems, but which is, at the same time, less expensive.

Furthermore, the need is felt to provide a device for measuring the water content of the ground, vegetation and snow which is capable of providing reliable data relating to a significantly large area.

In addition, the need is felt to provide a device and a method for measuring the water content of the ground and vegetation which is adapted to be used in agriculture for the so-called precision irrigation.

Such needs are met by a device for measuring the water content of the ground, vegetation and snow in accordance with claim 1, and by a method for measuring the water content of the ground, vegetation and snow according to claim 16.

DESCRIPTION OF THE DRAWINGS

Further features and advantages of the present invention will become more apparent from the following description of the indicative and non-limiting embodiments thereof, in which.

The common elements or parts of elements among the embodiments described below will be indicated with the same reference numerals.

DETAILED DESCRIPTION

Figure 1:
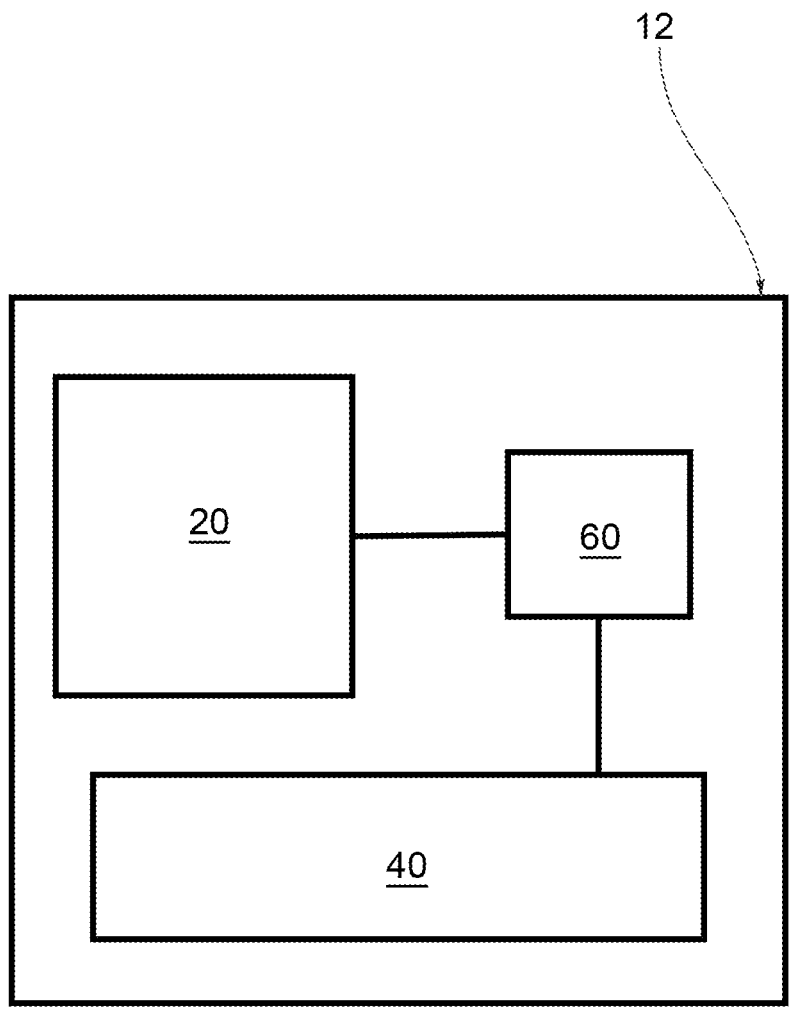
FIG. 1 diagrammatically shows a device for measuring the water content of the ground according to the present invention.
Figure 2:
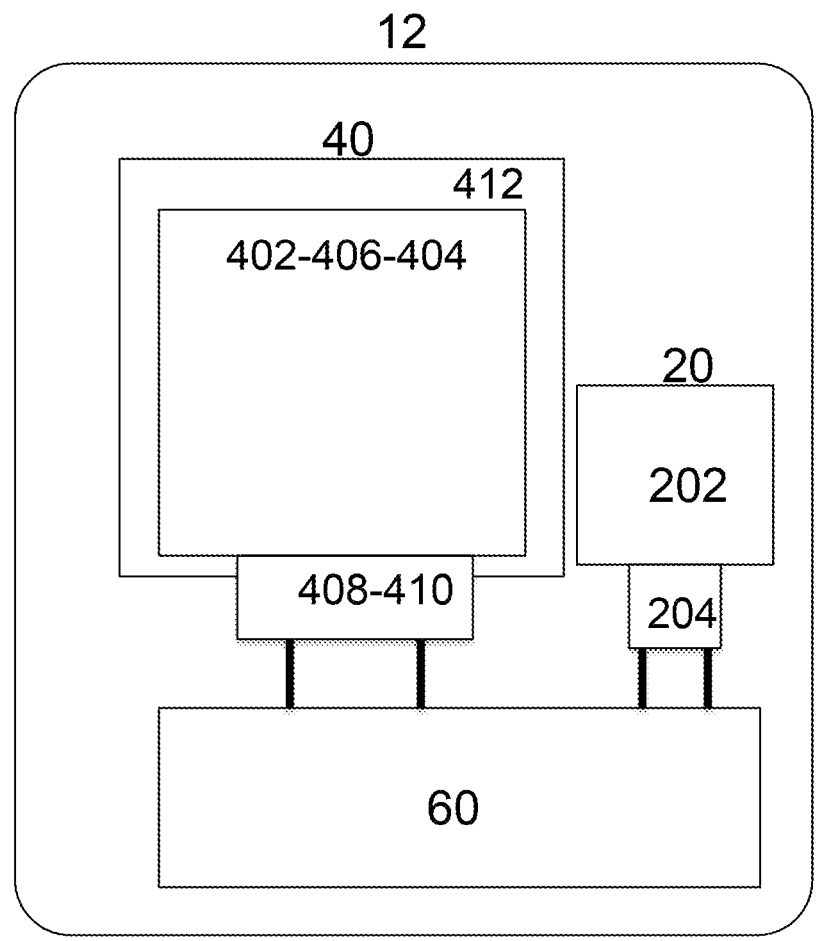
FIG. 2 diagrammatically shows an alternative embodiment of a device for measuring the water content of the ground according to the present invention.

FIG. 1 diagrammatically shows as a whole a device for measuring the water content of the ground, vegetation and snow (hereinafter also referred to as device), which is indicated with reference numeral 12.

The device 12 comprises at least one first module 20 adapted to measure a flow of cosmic rays incident to the ground and at least one second module 40 adapted to measure a flow of ambient neutrons.

The device further comprises a control unit 60 connected to the at least one first module 20 and to the at least one second module 40. The control unit 60 is adapted to process the measurements of the at least one first module 20 and of the at least one second module 40 to determine the measurement of the water content.

In particular, the device 12 is particularly adapted to measure the water content of the ground, vegetation or snow.

In accordance with a possible embodiment, the first module 20 comprises a first module scintillator 202, and at least one first module light meter 204, adapted to measure the light emitted by the first module scintillator 202.

As known, the scintillator is a material capable of emitting light pulses, in the visible or ultraviolet spectrum, when it is crossed by high energy photons or by charged particles, and therefore also by the incident flow of cosmic rays.

For measuring the flow of incident cosmic rays, by means of the detection of high energy neutrons [E>2 MeV], protons and muons, the use of a plastic scintillator was found to be particularly advantageous. For example, a scintillator of this type is the one marketed under the name EJ-200 by Eljen Technology.

In accordance with a possible embodiment, the at least one first module light meter 204 adapted to measure the light emitted by the first module scintillator 202 may be a silicon photomultiplier, also known as SiPM (Silicon PhotoMultiplier).

As is known, silicon photomultipliers are produced directly from a layered silicon structure on which matrices consisting of arrays of microcells are arranged on a silicon substrate. Each microcell is a single photon avalanche photodiode (or APD).

The photomultipliers of the SiPM type have volumes, weight, consumption rates and prices which are much lower with respect to conventional photomultipliers with vacuum tubes. They are also extremely robust from a mechanical point of view and do not require a high voltage power supply (about 1000 V) typical of the photomultiplier tubes.

As it will be explained below, the measurement of the flow of incident cosmic rays is used to normalize the measurement of ambient neutrons with respect to the variations of the incident flow of cosmic rays.

In accordance with a possible embodiment of the present invention, the at least one second module 40 comprises: a first sheet 402 and a second sheet 404 at least partially made with a scintillator; and a light guide 406 interposed between the first sheet 402 and the second sheet 404. The second module 40 further comprises at least one second module light meter 408, 410 adapted to measure the light conveyed by the light guide 406.

In accordance with a possible embodiment, the second module 40 provides for the use of a polyethylene coating 412, 414. The coating may comprise a lower sheet 412 and an upper sheet 414, at least partially covering the first sheet 402 and the second sheet 404.

The polyethylene, which the coating is made of, may be of high or low density, and may have a thickness varying between 1 and 10 cm. The function of the coating is to moderate the energy of the ambient neutrons.

The first sheet 402 and the second sheet 404 may comprise scintillator crystals in a silicone-based matrix.

Advantageously, the first sheet 402 and the second sheet 404 may comprise scintillator crystals and Lithium-based crystals (for example, enriched Li-6) or Boron-based crystals (for example, enriched B-10), in a silicone-based matrix.

The silicone matrix ensures a greater mechanical resistance of the scintillator sheets and a better heat resistance with respect to other types of matrices.

In accordance with a possible embodiment, the first sheet 402 and the second sheet 404 comprise scintillator crystals ZnS(Ag).

The light guide 406 may be made as a WLS solid plate, or as a WLS optical fiber bundle.

With WLS it is meant a material which, when hit by a certain wavelength, emits a different wavelength.

The wavelength shift reduces the self-absorption effects in the emitter material and allows to effectively transport the scintillation light up to the device 408 and 410.

Figure 3:
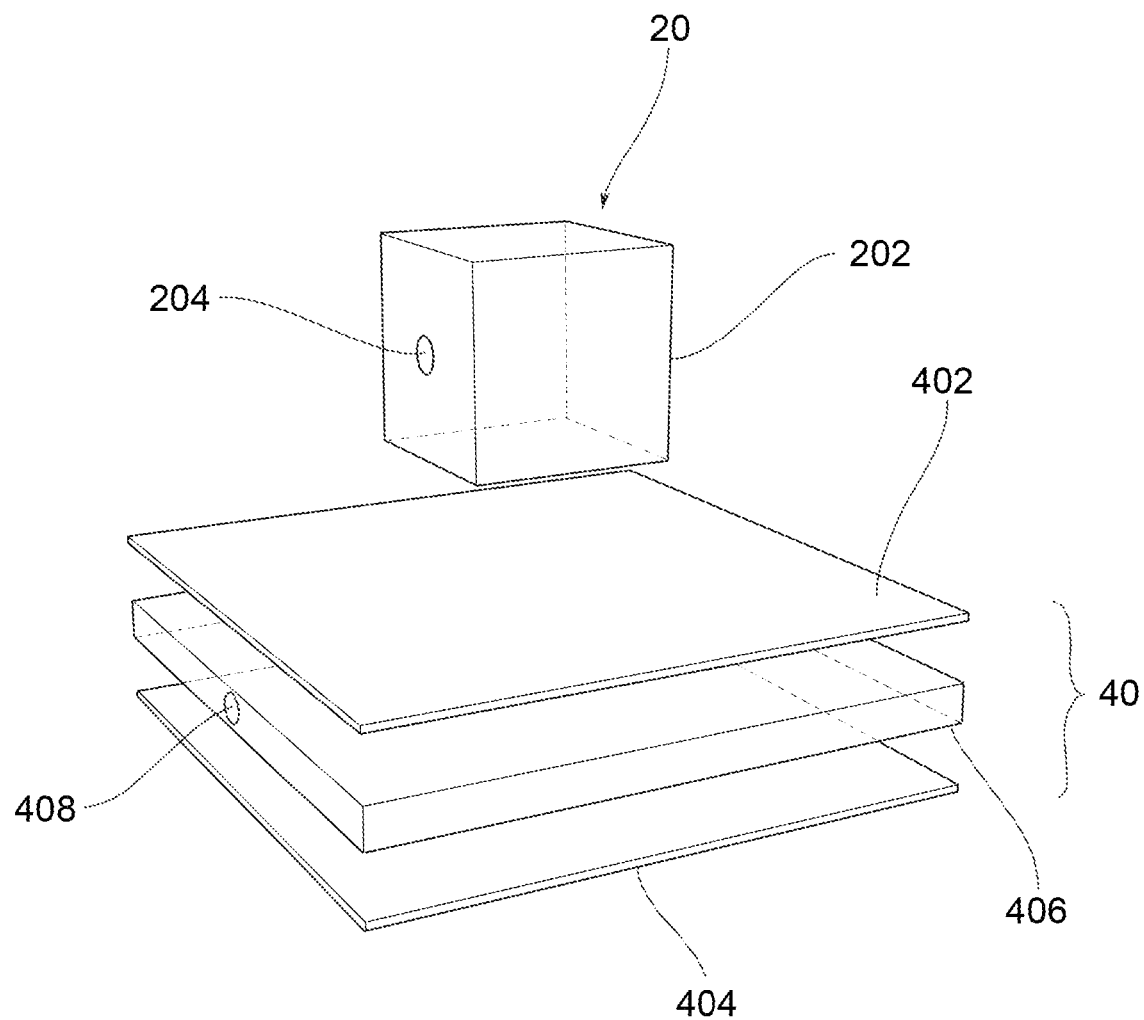
FIG. 3 diagrammatically shows some components of a device according to the present invention in a partially exploded view.
Figure 4:
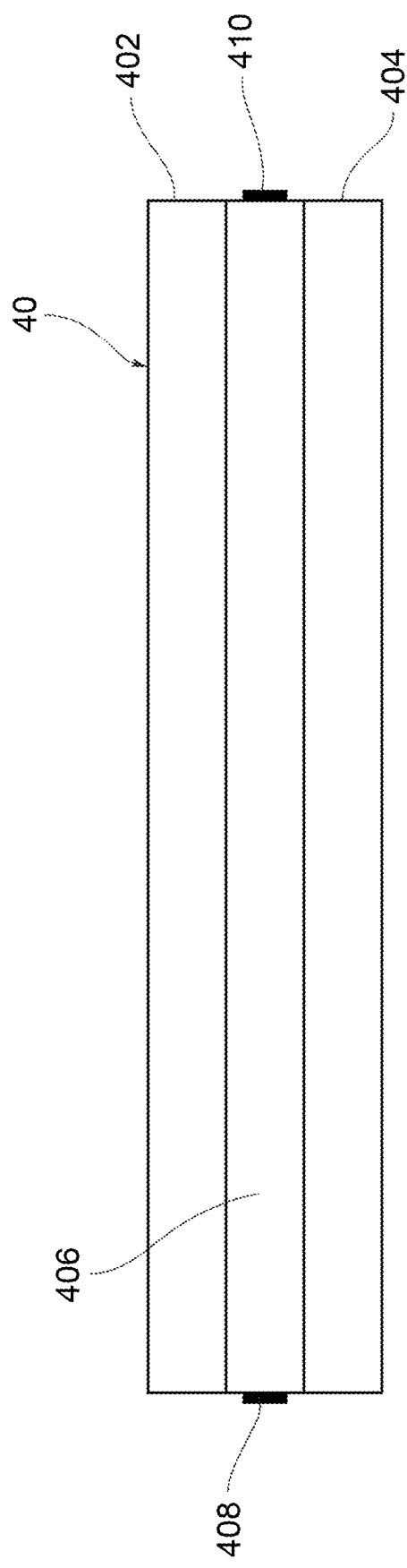
FIGS. 4 and 5 diagrammatically show a side view and a front view of a component of a device according to the present invention.
Figure 5:
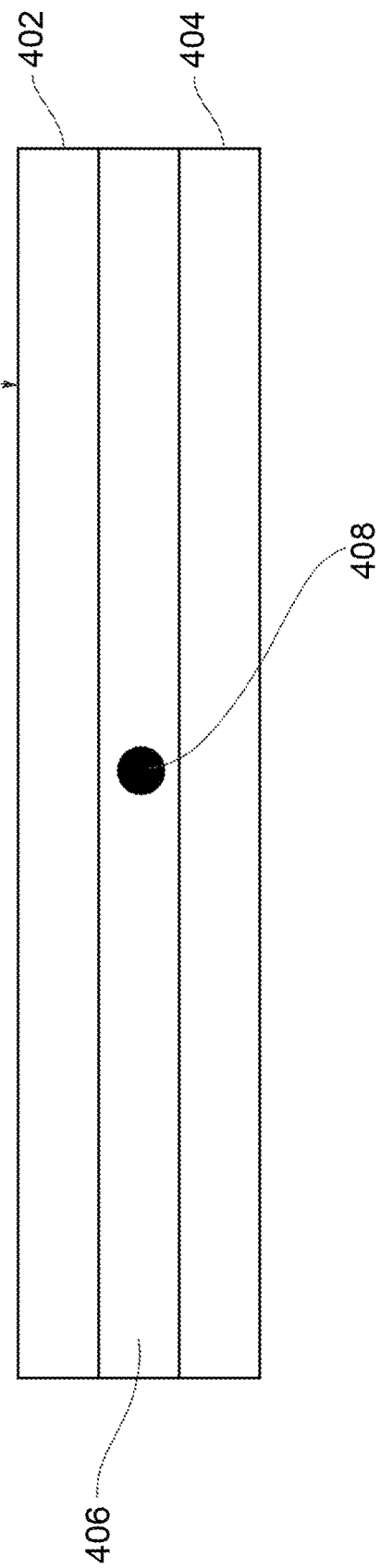
Figure 6:
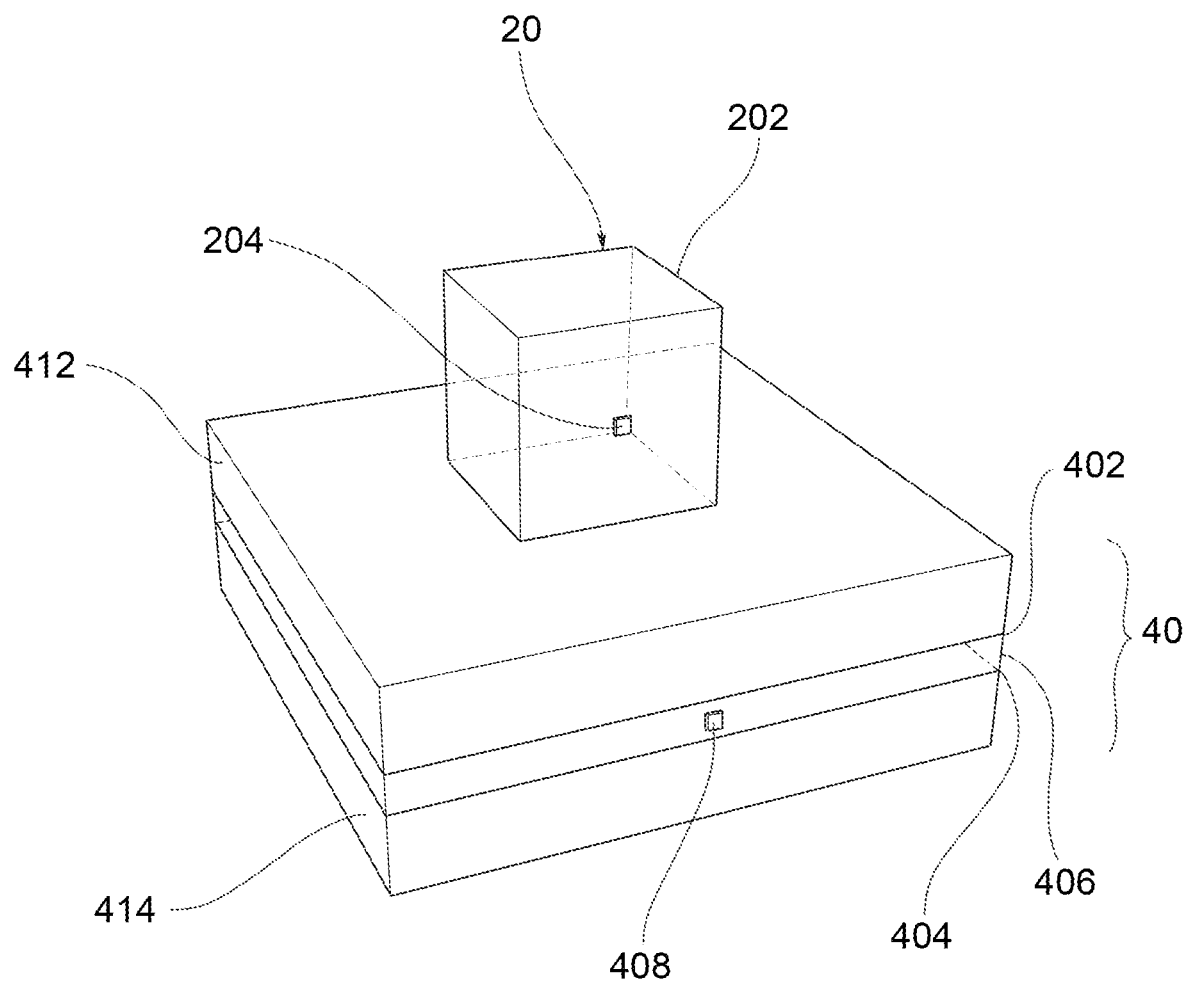
FIG. 6 diagrammatically shows some components of a device according to the present invention.
Figure 7:
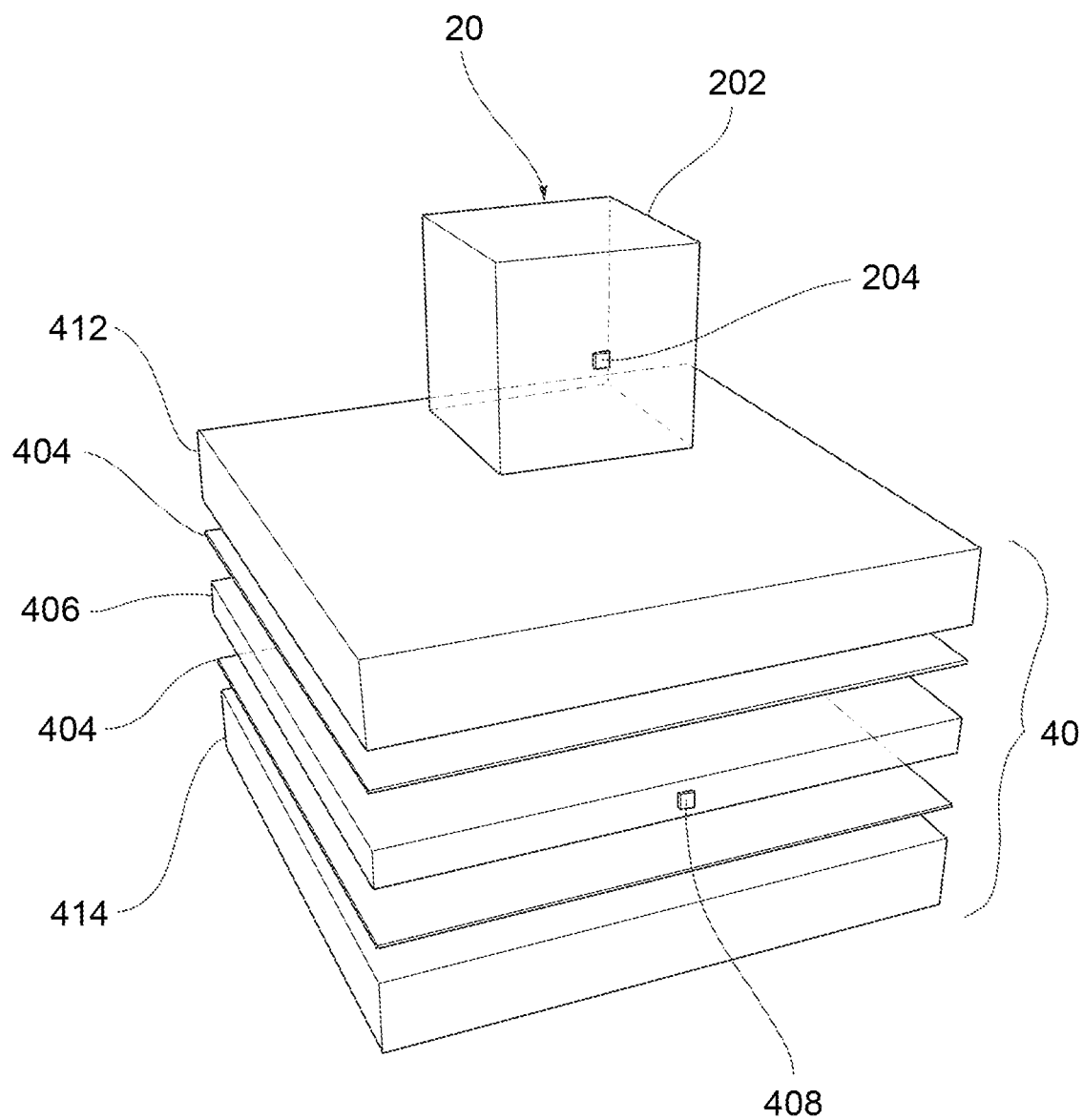
FIG. 7 diagrammatically shows some components of the device of FIG. 5 in a partially exploded view.

Advantageously, the second module 40 may comprise two second module light meters 408, 410 adapted to measure the light conveyed by the light guide 406. In accordance with a possible embodiment, shown in the example of FIG. 3, the two light meters 408, 410 may be arranged at two opposite sides of the light guide 406.

In accordance with a possible embodiment, the at least one second module light meter 408, 410 adapted to measure the light conveyed by said light guide 406 is a silicon photomultiplier (SiPM). Advantageously, the second module silicon photomultiplier is substantially the same as the first module.

In the embodiments shown in the attached Figures, the first module 20 which measures the muon flow uses a single SiPM, while the second module 40 which measures the ambient neutrons preferably uses two SiPMs and therefore two reading points, so as to drastically reduce the electronic noise of the SiPM even at low thresholds.

The first sheet 402 and the second sheet 404 have a substantially square position having a length of the side between 100 mm and 200 mm and a thickness between 0.2 mm and 2 mm.

Advantageously, the part of the sensors may be conceived modularly, so as to be possible to add, on request, other modules for measuring the ambient neutron flow, so as to increase the detection efficiency and reduce measurement times.

In accordance with a possible embodiment, the device may comprise an electrical power supply (not shown) with at least one solar panel and a back-up battery.

Advantageously, the device has dimensions equal to or less than a cube having a side of 400 mm.

The device may be waterproof, in particular it may be (IP65).

In the modular logic of the device, the control unit may be a dedicated card containing a series of channels with standard components to discriminate and integrate the electrical signals produced by the SiPMs. The card also provides low-voltage SiPM power supply (a few tens of volts) with a feedback system to compensate for deviations due to temperature changes.

Advantageously, the card may be adapted to accommodate the electronics required for multiple neutron flow measurement modules.

The signals selected by the control units may be digitized and read by a low consumption Linux micro PC (Raspberry PI, Beaglebone or equivalent), which processes them in real time using dedicated pulse shape analysis software.

The device 12 may also be provided with a remote connection module (not shown) which allows sending the processed data externally, by means of a Wi-Fi connection or equivalent, i.e., GSM, to an external server.

The method for measuring the water content comprises the steps of:
  providing a device 12 for measuring the water content comprising: at least one first module 20 adapted to measure the flow of incident cosmic rays, i.e., of high energy neutrons, protons and muons originating from the interactions of primary cosmic rays with the high layers of the atmosphere;
at least one second module 40 adapted to measure the ambient neutron flow; and a control unit 60 connected to the at least one first module 20 and to the at least one second module 40.

The method further comprises a step of processing the measurements made by the first module 20 and by the second module 40 by means of the control unit 60 to obtain a measurement of the water content, obtained from the measurement of the ambient neutron flow normalized with respect to the measurement of the flow of incident cosmic rays.

In particular, the method is particularly adapted to measure the water content of the ground, vegetation or snow.

Therefore, the advantages which may be achieved with the present invention are now evident.

In particular, the device and the method allow to measure the number of epithermal-slow neutrons and also to measure the primary flow of cosmic rays, essential for the correct normalization of the data.

The device is in fact autonomous, in particular it does not need to reprocess the data after having downloaded the information on the flow of incident cosmic rays from the research centers which make them available, possibly with several hours or days of delay. The measurement is therefore substantially in real time.

The water content information provided by the device covers a spatial and temporal resolution gap which is missing in the market. In fact, the systems of the background art move from electromagnetic sensors, which provide instantaneous data, but relating to a volume not exceeding one decimeter, to satellite systems with resolutions in the range of kilometers and a temporal resolution of one or more weeks.

The device of the present invention is adapted to measure the water content of some hectares in a time which varies between an hour and a day. Furthermore, it averages the data even in depth, up to 50-60 cm.

Thereby, the issue of satellite detections which give purely superficial information is overcome.

The data provided, therefore, is the missing information on the ground water content on the hectare range and overcomes the issue of the inhomogeneity of the ground which prevents the use of electromagnetic probes for this purpose.

The present device may be used for example for:
  research in the hydrogeological/climatological field: measurement of the ground water content validating forecast models with short- and long-term monitoring;
  research in the snow/glaciological field: monitoring of the water content in the snow-glacial basin; the monitoring of this data is interesting especially in spring, to know the water availability and to monitor possible unexpected floods caused by sudden melting of the snowpack.
  climatological monitoring: long-term monitoring of local climate variability.
  precision irrigation: knowledge of the ground water content to optimize the humidity present in the ground so as to minimize the need for treatments, i.e., irrigation, and maximize agricultural production.

Those skilled in the art, in order to satisfy specific needs, may modify the embodiments described above and/or replace elements with other functionally equivalent, without departing from the scope of the following claims.

The invention claimed is:

1. A device for measuring the water content of the ground, vegetation and snow, comprising:
  at least one first module adapted to measure the flow of incident cosmic rays in the form of high energy neutrons, protons and muons originating from interactions of cosmic rays with high layers of the atmosphere;
  at least one second module adapted to measure an ambient neutron flow, between epithermal and slow; and
  a control unit connected to said at least one first module and to said at least one second module;
  wherein said control unit is adapted to process the measurements of said at least one first module and said at least one second module to determine the measurement of the water content of the ground, vegetation and snow.

2. The device according to claim 1, wherein said first module comprises a first module scintillator; and at least one first module light meter adapted to measure the light emitted by the first module scintillator.

3. The device according to claim 2, wherein said first module scintillator is a plastic scintillator.

4. The device according to claim 2, characterized in that said at least one first module light meter adapted to measure the light emitted by the first module scintillator is a silicon photomultiplier.

5. The device according to claim 2, characterized in that said second module comprises: a first sheet and a second sheet at least partially made with a scintillator; being a light guide interposed between said first sheet and said second sheet; said second module further comprising at least one second module light meter adapted to measure the light conveyed by said light guide.

6. The device according to claim 2, wherein the second module provides for the use of a polyethylene coating for the purpose of moderating the energy of ambient neutrons.

7. The device according to claim 5, wherein said first sheet and said second sheet comprise scintillator crystals in a silicone-based matrix.

8. The device according to claim 5, wherein said first sheet and said second sheet comprise scintillator crystals and Lithium or Boron-based crystals in a silicone-based matrix.

9. The device according to claim 5, wherein said first sheet and said second sheet comprise ZnS (Ag) scintillator crystals.

10. The device according to claim 5, wherein said light guide is a WLS solid plate or a WLS optical fiber bundle.

11. The device according to claim 5, wherein said second module comprises two second module light meters adapted to measure the light conveyed by said light guide.

12. The device according to claim 5, wherein said at least one second module light meter adapted to measure the light conveyed by said light guide is a silicon photomultiplier.

13. The device according to claim 5, wherein said first sheet and said second sheet have a substantially square position having a length of the side between 100 mm and 200 mm and a thickness between 0.2 mm and 2 mm.

14. The device according to claim 5, wherein the device further comprises an electrical power supply with at least one solar panel and a back-up battery.

15. The device according to claim 5, wherein the device has dimensions equal to, or less than a cube having a 400 mm side.

16. A method for measuring the water content of the ground, vegetation and snow, comprising the steps of:
providing a device for measuring the water content of the ground, vegetation and snow comprising: at least one first module adapted to measure the flow of incident cosmic rays in the form of high energy neutrons, protons and muons originating from interactions of cosmic rays with high layers of the atmosphere; at least one second module adapted to measure ambient neutron flow; and a control unit connected to said at least one first module and said at least one second module; and processing the measurements made by the first module and the second module using the control unit to obtain a measurement of the water content of the ground, vegetation and snow;

wherein the measurement of the water content of the ground, vegetation and snow is obtained from the measurement of a normalized ambient neutron flow with respect to the measurement of the flow of cosmic rays incident to the ground.

17. The device according to claim 3, wherein the second module provides for the use of a polyethylene coating for the purpose of moderating the energy of ambient neutrons.

18. The device according to claim 1, wherein the device further comprises an electrical power supply with at least one solar panel and a back-up battery.

19. The device according to claim 1, wherein the device has dimensions equal to, or less than a cube having a 400 mm side.

* * * * *